United States Patent [19]
Sutter et al.

[11] Patent Number: 5,368,483
[45] Date of Patent: Nov. 29, 1994

[54] DEVICE-FOR FIXING A DENTAL PROSTHESIS TO A JAW BONE

[75] Inventors: Franz Sutter, Niederdorf; Ulrich Mundwiler, Tenniken, both of Switzerland

[73] Assignee: Institut Straumann AG, Waldenburg, Switzerland

[21] Appl. No.: 95,119

[22] Filed: Aug. 20, 1993

[51] Int. Cl.$^5$ .............................................. A61C 8/00
[52] U.S. Cl. ..................................................... 433/173
[58] Field of Search ............... 433/172, 173, 174, 175, 433/176

[56] References Cited

U.S. PATENT DOCUMENTS

| | | | |
|---|---|---|---|
| 5,026,285 | 6/1991 | Durr et al. | 433/173 |
| 5,116,225 | 5/1992 | Riera | 433/174 |
| 5,125,840 | 6/1992 | Durr et al. | 433/173 |
| 5,135,395 | 8/1992 | Marlin | 433/173 |
| 5,246,370 | 9/1993 | Coatoam | 433/173 |

FOREIGN PATENT DOCUMENTS 9108713  6/1991  WIPO ................................ 433/174

OTHER PUBLICATIONS

"Bonefit Basic Information" pp. 1-6, Institute Strauman.
"The New Concept of ITI Hollow-Cylinder and Hollow Screw Impants:" 1988 Franz Sutter/Andre Schroeder, DDS, PhD Daniel A. Buser, DDS pp. 161-172.
"Journal of Oral Implantalogy" vol. XVI, No. 4, 1990 pp. 297-301.

*Primary Examiner*—John J. Wilson
*Attorney, Agent, or Firm*—Anderson Kill Olick & Oshinsky

[57] ABSTRACT

The device for fixing a dental prosthesis has a base which can be inserted into a jaw bone, an abutment and a shell. The base has a hole with a mouth at its end face, with an internal thread and with an extension and has a conical annular surface enclosing the mouth of the hole. The abutment has a thread part which passes through the shell in the assembled device and is screwed into the internal thread of the base, and an outer part located outside the base and serving for holding a dental prosthesis. In the assembled device, the shell fits into the extension of the hole and rests with a conical outer surface firmly against a conical inner surface of the base. Furthermore, the outer part of the abutment rests with a conical stop surface firmly against the annular surface of the base. In the assembled device, the abutment is connected to the base in a stable manner and covers its end face without leaving gaps.

31 Claims, 5 Drawing Sheets

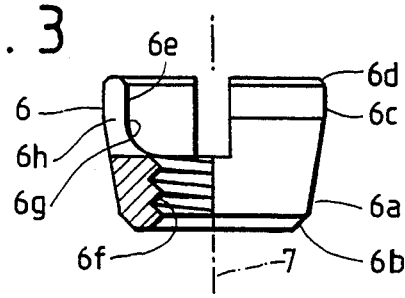
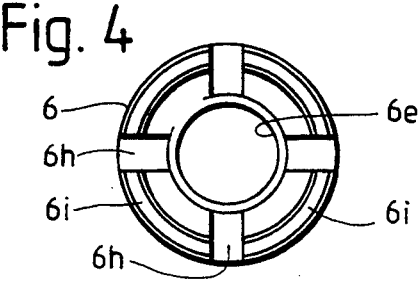
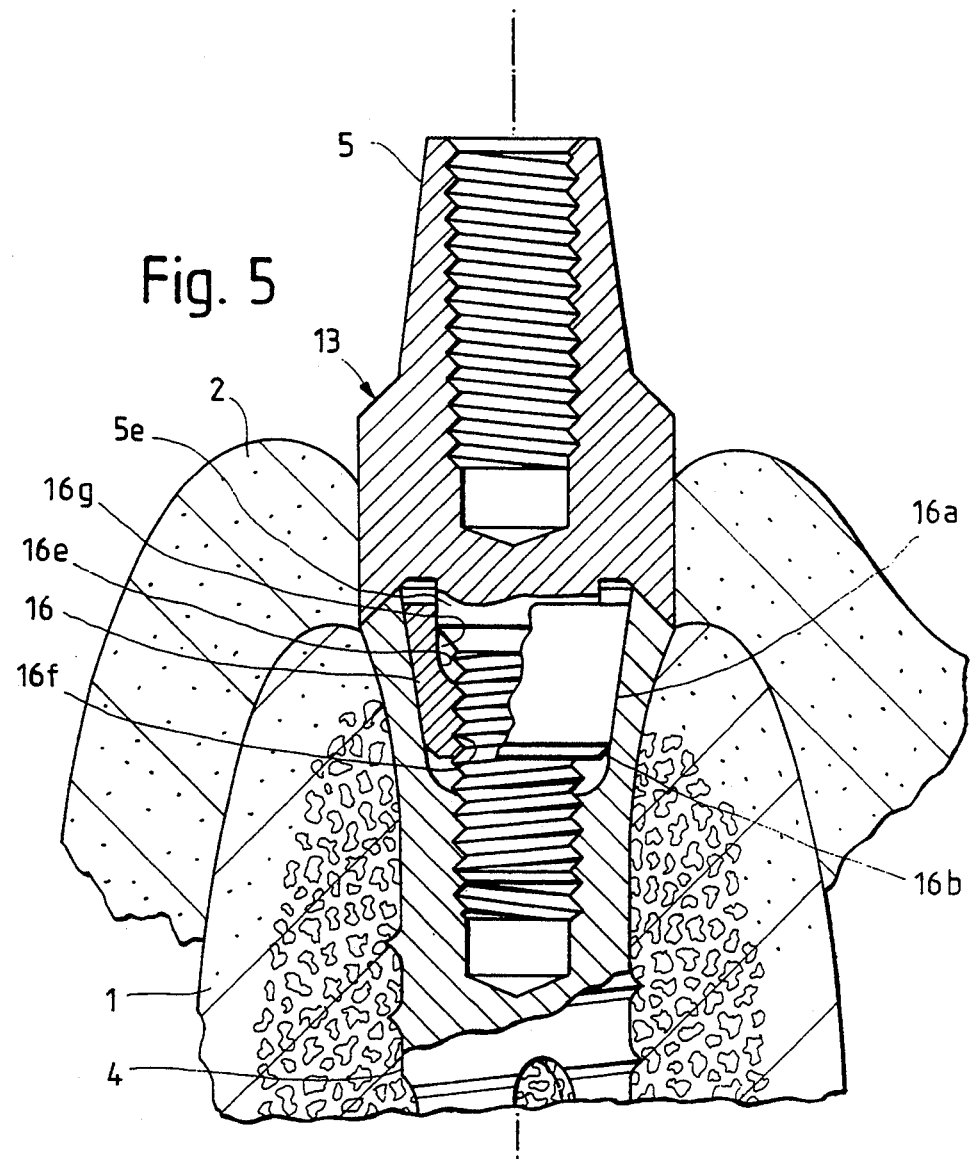

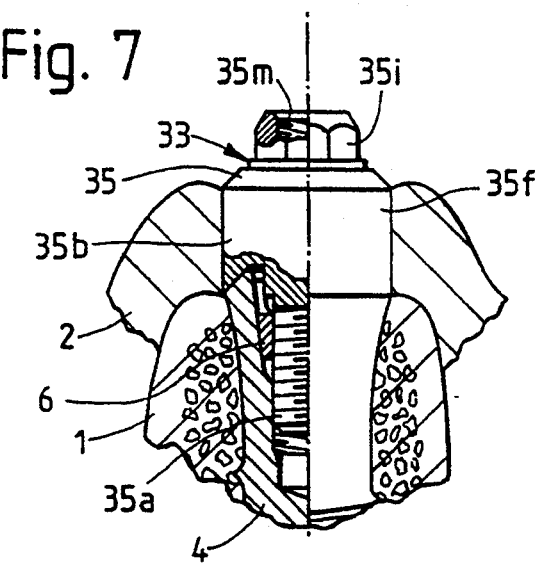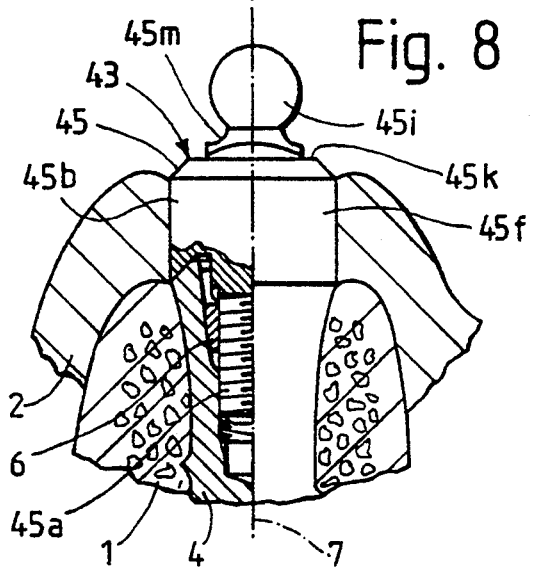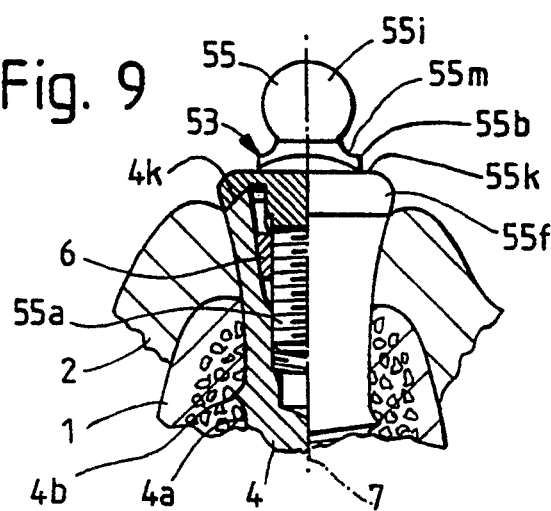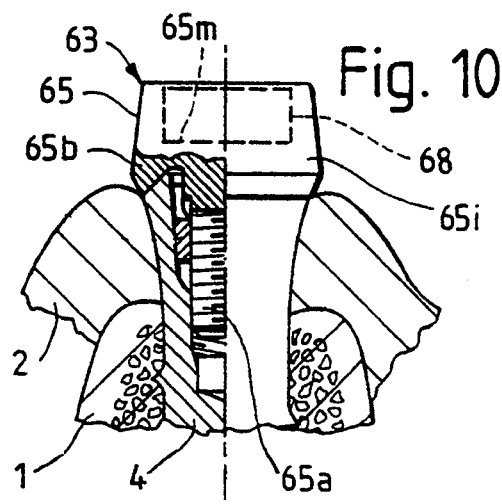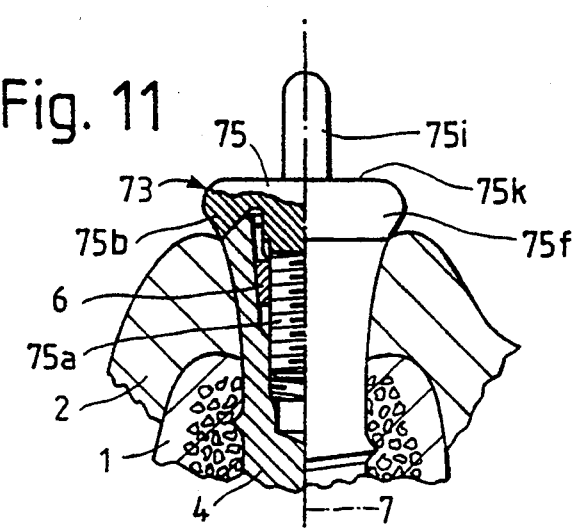

DEVICE-FOR FIXING A DENTAL PROSTHESIS TO A JAW BONE

BACKGROUND OF THE INVENTION

1. Field of the Invention

The invention relates to a device for fixing a dental prosthesis to a jaw bone.

A device of this type can be used, for example, for fixing a dental prosthesis which consists of a single, artificial tooth usually composed of a plurality of parts. However, it is also possible to insert two or more devices of the stated genera into one and the same jaw bone, which then together hold a dental prosthesis which forms a group of two or more artificial teeth, and namely, for example, a so-called bridge or an entire prosthetic denture.

2. Description of the Prior Art

Devices known under the trade name BONEFIT have two parts which can be detachably connected to one another, namely a base which can be anchored in the jaw bone and is also referred to as the implant or primary part and an abutment which serves for holding the dental prosthesis and is also referred to as the secondary part. The base is elongated and has an axial blind hole which has a mouth at the end face of the base, which face is opposite the dental prosthesis, and has there a mouth enclosed by an annular surface. The blind hole has a section provided with an internal thread and a conical extension extending away therefrom to the end face. The abutment has an inner part with a thread part possessing an external thread, and with a thick part extending conically away from said thread part. Furthermore, the abutment has an outer part adjacent to the thicker end of the thick part. When the device is in the assembled state, the inner part of the abutment is present in the hole of the base, the thread part of the abutment being screwed to the internal thread of the base and the conical thick part of the abutment fitting firmly in the conical extension of the base. The outer part of the abutment is then outside the base and can project into a dental prosthesis and carry this as well as hold it firmly. In the known BONEFIT devices, the abutment section which is located directly above the end face of the base is usually cylindrical or slightly conical and, together with the inclined annular surface present on the end face of the base, forms a shoulder or neck.

The BONEFIT devices have proven very suitable for applications in which the end face of the base is approximately flush with that surface of the gingiva facing away from the jaw bone, or projects slightly out of the gingiva and is in a supragingival position, and in which a dental prosthesis rests on the shoulder or neck. However, if the abutment has, for example, a retentive anchor for clipping on a denture, an intermediate space may be present between said head and the shoulder. The transverse forces exerted on the denture and other forces must then be transmitted to the base or primary part exclusively by the thread part and the conical thick part of the abutment or secondary part, which may cause undesirably large local stresses. In addition, the gingiva may grow over the shoulder or neck so that pockets which are difficult to clean and in which bacteria may develop form under certain circumstances. Furthermore, and in particular, it would be advantageous in various problem cases to cover the base after insertion completely with the gingiva during a certain healing period. In order to permit covering of the base, the latter can of course be inserted into the jaw bone so deeply that its end faces are approximately flush with the ridge of the jaw bone and can then be temporarily closed with a closure screw. If the gingiva is cut open again after the healing period, the closure screw is removed and the abutment is screwed into the base, the stated shoulder or neck is present below the gingiva after the latter has healed. If the dental prosthesis usually produced by a dental technician thereafter does not fit very exactly and without gaps on the shoulder or neck, there is a considerable danger that free cavities will remain in the shoulder or neck under the gingiva and bacteria will develop in the said cavities. These may interfere with the healing process and cause infections.

In the "Journal of Oral Implantology", Volume XVI, 1990, No. 4, pages 297–301, a device having a base or implant, a connecting element, a spacing shell and an abutment is disclosed. The base is identical or similar to that in the BONEFIT devices. The connecting element has a thinner and a thicker thread part, each having an external thread, a cone present between the two thread parts and an axial threaded hole. The spacing shell has an axial through-hole with an internal thread. The abutment has a thread part with an external thread.

When this device is used, the base can be inserted into a hole in the jaw bone in such a way that the end face of the base is approximately flush with the surface of the jaw bone. After healing of the bone, the thinner thread part of the connecting element can be screwed into the base until the cone of the connecting element fits firmly in the conical extension of the hole of the base. Thereafter, the spacing shell can be screwed onto the thicker thread part of the connecting element, which thread part projects from the base, and the thread part of the abutment can be screwed into the threaded hole of the connecting element. The spacing shell then rests firmly against the end face of the base.

This device disclosed in the "Journal of Oral Implantology" has already proven its worth but has the disadvantage that it has four separate parts, some of which have relatively complicated shapes and in particular possess many threads. The production and assembly of this device are therefore relatively expensive and complicated.

SUMMARY OF THE INVENTION

It is therefore the object of the invention to provide a device which can avoid disadvantages of the known devices and in particular ensures stable connection of the abutment to the base and very substantially prevents the development of bacteria in the region of the point of emergence of the abutment from the base, the device being economical to produce and simple to assemble.

This object is achieved by a device for fixing a dental prosthesis to a jaw bone, having a base intended for insertion into a hole in the jaw bone and an abutment which can be connected to said base and is intended for holding the dental prosthesis outside the jaw bone, the base having an end face, a hole with a mouth located at the end face, with an internal thread and with an extension widening from said internal thread to the end face and being bordered at least partly by a conical inner surface, and having an annular surface enclosing the mouth of the hole, and the abutment possessing an inner part which is intended for arrangment in the hole of the base and has an external thread intended for screwing to the internal thread of the base and an outer part nondetachably connected to the inner part and intended for arrangement outside the base, wherein a shell with an axial through-hole and with a conical outer surface intended to be adjacent to the conical inner surface of the base is present, wherein the inner part of the abutment can be screwed through the hole with the internal thread of the base and wherein the outer part of the abutment is designed for resting against the annular surface.

The base of a device according to the invention can be used, for example, in a jaw bone in such a way that its end face is approximately flush with the surface of the jaw bone. After insertion into the jaw bone and before the abutment is connected to it, the base can then be completely covered with the gingiva during a certain healing period. Such a completely subgingival arrangement of the base is very advantageous, for example, when, owing to a tumor of the jaw bone, a piece thereof is replaced by a transplant—i.e. a bone fragment taken from another bone—and a base is inserted into such a transplant or into a highly atrophied jaw bone. The complete coverage of the base by the gingiva then helps to avoid infections and permits rapid, complete healing of the jaw bone and good intergrowth of the latter with the base.

However, the base can also be inserted into a jaw bone in such a way that it projects therefrom and at least substantially passes through the gingiva after the latter have healed, so that the end face of the base is approximately flush with the limit of the gingiva facing away from the ridge of the jaw bone or is located outside the gingiva and thus in a supragingival position.

If the abutment of a device according to the invention is connected to the base, it rests against the annular surface of the base, which surface is present on the end face of said base. Both in the subgingival and in the supragingival position of the end face of the base, the abutment can be designed in such a way that it completely covers the end face of the base and has a lateral surface section which is rotationally symmetrical with respect to the axis of the device and abuts the lateral and/or outer surface of the base at the outer edge of the annular surface of the base without a joint and without a gap.

In a device intended for the subgingival arrangement of the base, that lateral surface section of the abutment which is located closest to the end face of the base in the assembled device and abuts the outer edge of the annular surface of the base preferably consists of a surface which completely penetrates the gingiva and is smooth, i.e. has no edges between its ends.

The stated lateral surface section of the abutment may be, for example—particularly in the case of a subgingival position of the end face of the base—parallel to the axis of the device and cylindrical. However, particularly in the case of a supragingival position of the end face of the base, the stated lateral surface section may also be conical or may be curved in the axial section, in which case it makes an angle of, preferably, not more than about 30° with the axis of the device at its end adjacent to the base.

That lateral surface section of the base which is adjacent to the outer edge of the annular surface widens, preferably in a trumpet-like manner, toward the said edge and preferably makes an obtuse angle or possibly approximately a right angle with the annular surface enclosing the mouth of the hole of the base. The lateral surface section of the abutment, which section abuts the outer edge of the annular surface of the base when the device is assembled, preferably makes an acute angle with the annular surface of the base and a stop surface of the abutment, which surface is adjacent to said annular surface. The sum of the two stated angles is preferably at least 135°, even better at least 150° and preferably at most 180°. If the sum of the two angles is 180°, the abutting lateral surface sections of the base and of the abutment are then continuously adjacent to one another in the axial section.

BRIEF DESCRIPTION OF THE DRAWINGS

The subject of the invention is now illustrated with reference to embodiments shown in the drawings. In the drawings, FIG. 3 shows a separate representation of the shell, drawn partly in section and partly as a view, FIG. 4 shows a plan view of the shell end present in FIGS. 2 and 3, FIG. 5 shows a section, corresponding to FIG. 2, through a device having a differently designed shell, FIG. 7 shows a device which is drawn partly as a view and partly in section and whose abutment has a multiedged peg for holding the dental prosthesis, FIG. 8 shows a device which is drawn partly as a view and partly in section and whose abutment has a retentive anchor, FIG. 9 shows a representation of another device having a retentive anchor, FIG. 10 shows a device whose abutment contains a magnetic coupling element and FIG. 11 shows a device having an abutment formed for soldering on a dental prosthesis.

DESCRIPTION OF THE PREFERRED EMBODIMENTS

Figure 1:
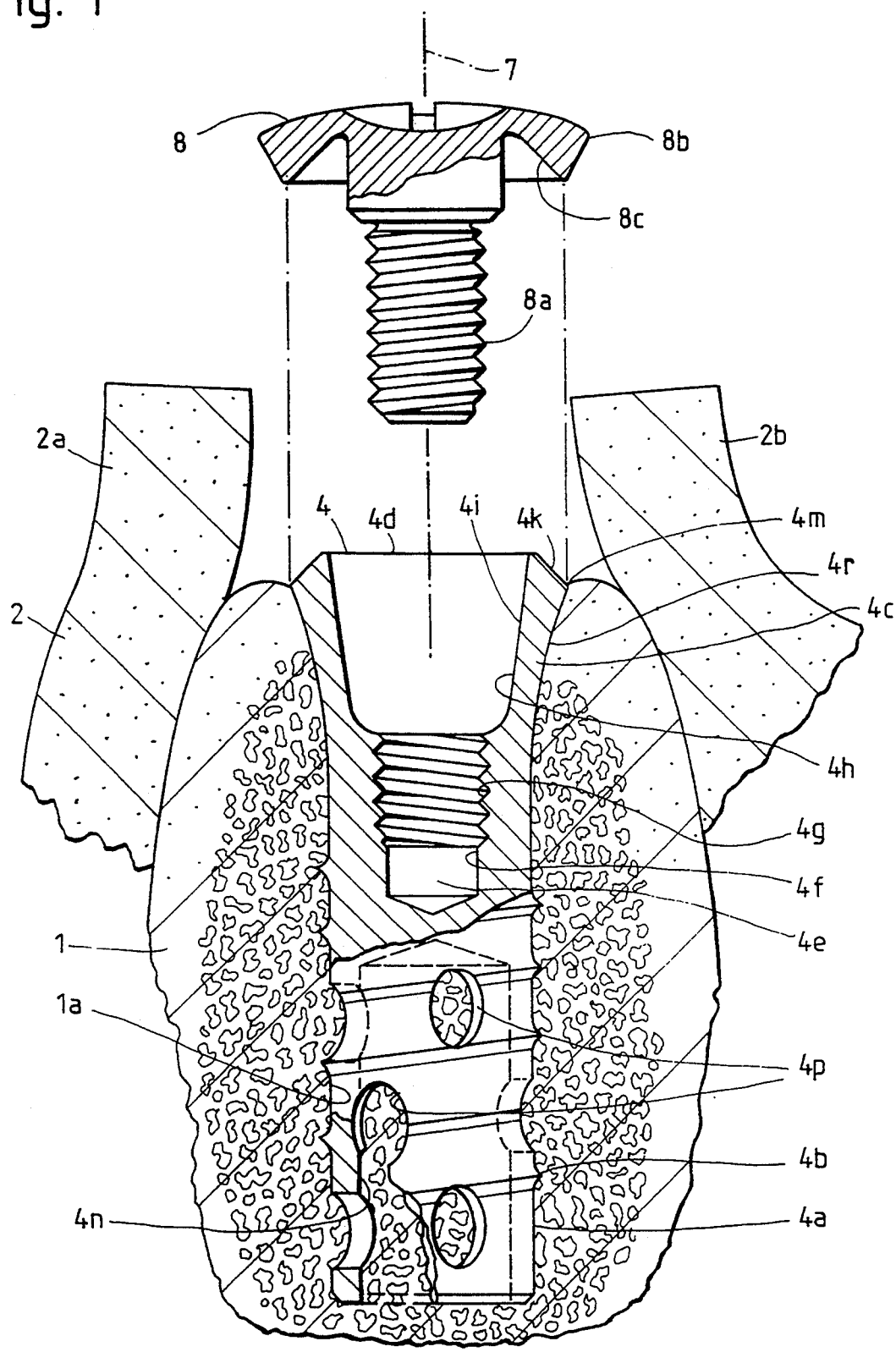
FIG. 1 shows a section through a jaw bone and a base of a device for fixing a dental prosthesis, said base being inserted into said jaw bone and a screw which serves for closing the hole in said base also being shown above the base.
Figure 2:
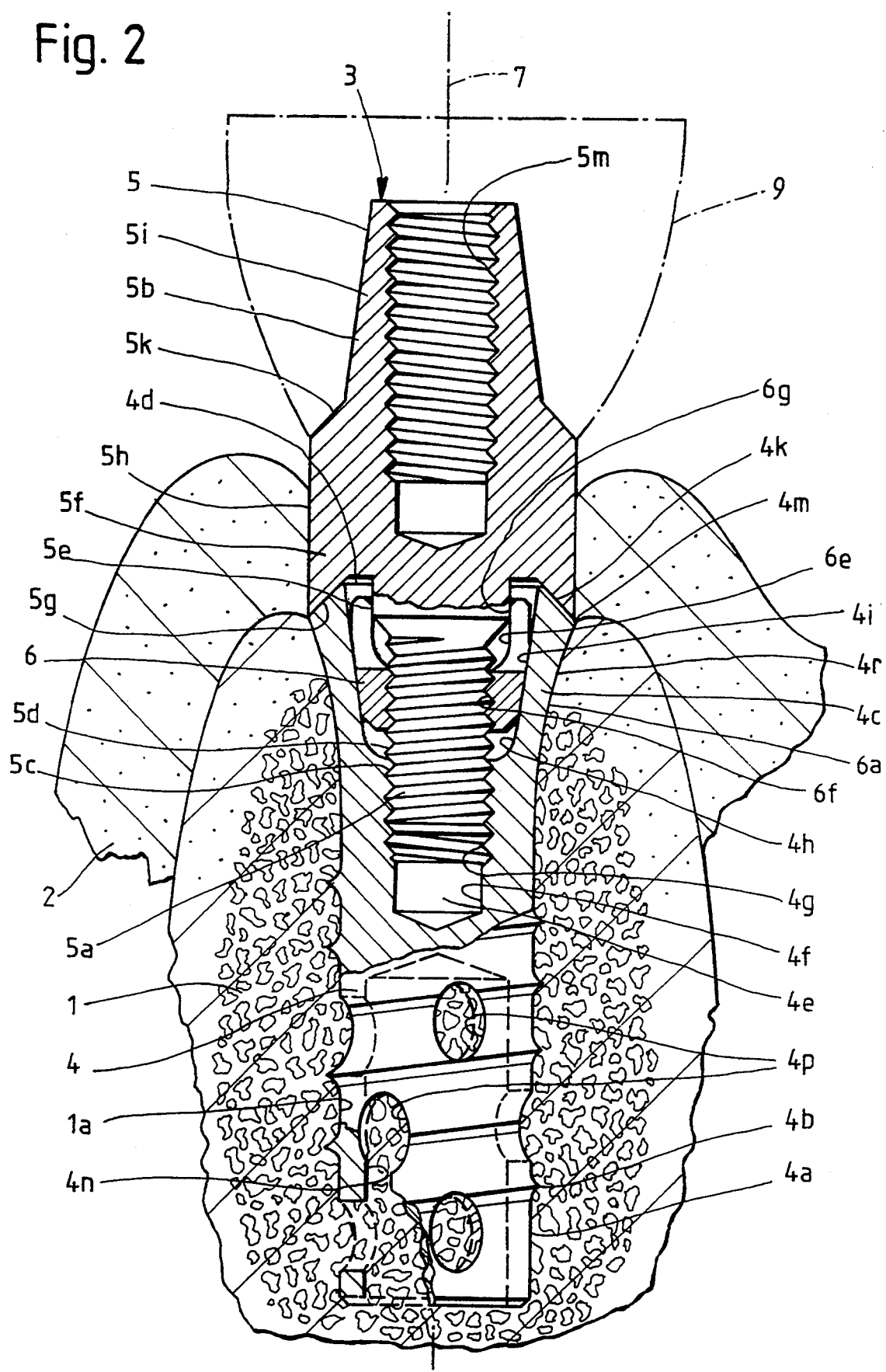
FIG. 2 shows a section through the jaw bone shown in FIG. 1 and a base and through an abutment screwed into said base and a shell present in the hole.

FIGS. 1 and 2 show a jaw bone 1 having a hole 1a entering its ridge. The hole 1a is in the form of a blind hole and has a base section which consists of an annular groove and is adjacent to a cylindrical bore which is hollow in the entire circular cross-section. An extension which widens toward the mouth and whose limiting surface is continuously curved in axial section is present between said bore and the mouth of the hole 1a. The bore section formed by the annular groove in the cylindrical bore is provided with an internal thread.

FIGS. 1 and 2 furthermore show the gingiva 2. Before the production of the hole 1a in the region of the jaw bone provided with the hole, the gingiva is cut open in such a way that gingiva flaps designated by 2a and 2b in FIG. 1 can be folded away. The hole 1a is then produced by drilling and cutting.

A device for fixing the dental prosthesis is designated as a whole by 3 in FIG. 2 and has three parts detachably connected to one another, namely a base 4 also shown in FIG. 1 and frequently designated the primary part or implant, an abutment 5 also designated, for example, as the secondary part and a shell 6. When the device 3 has been completely assembled, its three stated parts are generally rotationally symmetrical with respect to a common axis 7, which is therefore both the axis of the whole device and the axis of the base, of the abutment and of the shell.

The elongated base 4 has a cylindrical section 4a which is provided with an external thread 4b. Adjacent to the cylindrical section 4a is a section 4c which thickens in a trumpet-like manner away from said section 4a. In axial section, the lateral surface section 4r bordering said section 4c externally is uniformly and continuously curved, as in the case of the surface which borders the stated extension of the hole 1a. At its upper end most greatly inclined relative to the axis 7, the lateral surface section 4r of the section 4c makes an angle of at most 30° and, for example, about 15° to 25° with said axis. That end of the base 4 which is located in FIGS. 1 and 2 at the top on the free end of the thickening section 4c forms the end face 4d of said base. The base 4 is provided with a hole 4e which is coaxial with the axis 7, consists of a blind hole and has a mouth in the end face 4d. The hole 4e has a cylindrical base section 4f which is provided, at least in one part, with an internal thread 4g and therefore forms a threaded hole. The hole 4e has, between the internal thread 4g and the end face 4d, an extension 4h which widens toward said end face and is bordered, at least for the most part, by a conical inner surface 4i which makes an angle of, preferably, at least 5° and, preferably, at most 15° with the axis 7. The end face 4d is formed by an end face which encloses the mouth of the hole 4e and consists, at least for the most part, of an annular surface 4k which is inclined away from the axis 7 conically outward toward that end of the base which is opposite the end face 4d. The outer edge 4m of said annular surface also forms the outer edge of the end face 4d. The angle of inclination between the conical annular surface 4k and the axis 7 is about 20° to 70° and namely, for example, about 45°. The annular surface 4k makes an obtuse angle with that end of the lateral surface section 4r which is adjacent to the outer edge 4m of said annular surface, said lateral surface section being curved in axial section. The cylindrical section 4a of the base 4 furthermore has a hole 4n which is coaxial with the axis 7, consists of a blind hole and has a mouth at that end of the base 4 which is opposite the end face 4d. The cylindrical section 4a is furthermore provided with some holes 4p which pass through its lateral surface and enter the hole 4n. The base 4 consists of a one-piece member comprising a metallic material, namely titanium. The cylindrical section 4a is also provided with, for example, a coating applied by a plasma coating method and likewise consisting of titanium.

The elongated, one-piece, metallic abutment 5 which consists, for example, of titanium, has an inner part 5a and an outer part 5b. If the abutment 5 is connected to the base 4 in the assembled device according to FIG. 2, the inner part 5a is located in the hole 4e of the base 4 while the outer part 5b is arranged outside the base 4. The inner part 5a has a thread part 5c with an external thread 5d and an essentially cylindrical thick part 5e which is rotationally symmetrical with respect to the axis 7 and whose diameter is slightly larger than the external diameter of the external thread 5d. The thick part 5e is provided with a small bevel at its end facing the thread part 5c. The outer part 5d consists of an even thicker covering section 5f adjacent to the thick part 5e. Said covering section is bordered, at its end facing the base 4, by an annular surface, of which at least the outermost part serves as a conical stop surface 5g. This makes the same angle with the axis 7 as the annular surface 4k of the base 4 and rests against the annular surface 4k in the assembled device. The outer edge of the stop surface 5g and the cylindrical lateral surface section 5h of the covering section 5f, which lateral surface section is adjacent to this outer edge, have the same diameter as the outer edge 4m of the annular surface 4k. The lateral surface section 5h makes an acute angle with the stop surface 5g and, in the assembled device, also with the annular surface 4k of the base 4. The sum of this angle and the obtuse angle made by the surfaces 4k and 4r of the base is between 125° and 180° and is, for example, at least 150°. A conical end section 5i which tapers away from the covering section 5f is adjacent to said covering section. The conical lateral surface of said end section is connected at its further end by a likewise conical shoulder surface 5k to the cylindrical lateral surface section 5h of the covering section 5f and, together with the shoulder surface 5k, forms a shoulder having an obtuse angle in axial section. The length of the cylindrical lateral surface section 5h and the distance of the shoulder surface 5k from the stop surface 5g is preferably at least 2 mm, preferably up to about 5 mm and, for example, about 3 mm. The abutment 5 is also provided with an axial threaded blind hole 5m which has a mouth at the free end of the end section 5i.

The one-piece, metallic shell 6 which is shown separately in FIGS. 3 and 4 and consists, for example, of titanium has, in its middle region, a conical outer surface 6a which widens in an upward direction in FIGS. 2 and 3 and makes the same angle with the axis 7 as the conical inner surface 4i of the base 4. A bevel 6b which tapers toward the lower end of the shell 6, is likewise conical but makes a larger angle with the axis 7 is adjacent to that end of the conical outer surface 6a which is located at the bottom in FIGS. 2 and 3. A cylindrical outer surface 6c which has the same diameter as the further end of the conical outer surface 6a is adjacent to the upper end of the conical outer surface 6a. A bevel 6d which tapers toward the upper end of the shell is present on the upper end of the cylindrical surface 6c. The shell 6 has an axial through-hole 6e whose section located at the bottom in FIGS. 2 and 3 is provided with an internal thread 6f. The hole 6e has an extension 6g above the internal thread 6f. The boundary of said extension has a transition surface adjacent to the internal thread and arc-shaped in axial section, a cylindrical inner surface above said transition surface and, at the very top, a conical surface widening upward toward the mouth. The diameter of the cylindrical inner surface is slightly—for example about 0.01 mm to 0.05 mm—smaller than the diameter of the cylindrical surface of the thick part 5e of the abutment 5. Otherwise, the extension 6e extends from its end forming the upper mouth of the hole 6e into that region of the shell which is bordered on the outside by the upper end section of the conical outer surface 6a. That section of the lateral surface of the shell 6 which encloses the extension 6g is divided into a plurality of segments 6i, namely four such segments, which are uniformly distributed along the circumference of the shell, by slots 6h which are parallel to the axis 7 and enter the upper end of the shell. Said segments are slightly elastically deformable so that they can be spread away from the axis 7, starting from the position which they assume in the relaxed state.

The insertion and assembly of the device 3 will now be explained.

If the gingiva 3 was cut open according to FIG. 1 and the jaw bone 1 provided with the hole 1a, the base 4 is inserted into the hole 1a and screwed into the internal thread of the hole 1a with the aid of an inserting tool. The base 4 adopts the position which is shown in FIG. 1 and in which the outer edge 4m of the annular surface 4k is located approximately at the edge of the mouth of the hole 1a. The end face 4d of the base 4 then projects, for example, slightly out of the hole 1a and/or is more or less exactly flush with that surface of the jaw bone 1 which encloses the hole 1a.

A closure screw 8 drawn above the base 4 in FIG. 1 has a thread part 8a, which can be screwed into the internal thread 4g, and a head 8b. This has, on its side facing the base 4, a conical surface 8c which makes the same angle with the axis 7 as the conical annular surface 4k and has the same external diameter as the latter. After insertion of the base 4 into the jaw bone 1, the screw 8 can be screwed into the hole 4e of the base 4 so that it rests with its conical surface 8c on the annular surface 4k of the base 4 and closes the hole 4e. The gingiva flaps 2a, 2b can then be placed over-the base 4 and the screw 8 and sutured. The base and the screw can then be left in the jaw bone 1 during a healing period or phase which lasts, for example, for a few months. The jaw bone can then heal and to a certain extent intergrow with the base 4 and in particular also grow through its holes 4p in the manner indicated in FIG. 2. During this healing period or phase, the gingiva 2 does of course also heal and grows together over the base.

After the envisaged healing period or phase has elapsed, the gingiva 2 can be cut open again and the screw 8 unscrewed from the base 4. Before the abutment 5 is connected to the base 4, the shell 6 is screwed onto the thread part 5c of the abutment 5 in such a way that the shell 6 is closer to the free end of the thread part than subsequently when the device has been completely assembled. The free end section of the abutment thread part 5c, which section projects from the lower end of the shell, is then screwed, with the aid of an insertion tool engaging the abutment, into that section of the hole 4e of the base 4 which is provided with the internal thread 4g. In this insertion process, the shell 6 is turned until its conical outer surface 6a rests firmly against the conical inner surface 4i of the base 4, and then remains in its axial position. The thread part 5c can also be screwed more deeply into the base 4 until the conical stop surface 5g of the abutment 5 rests against the annular surface 4k of the base 4. The cylindrical thick part 5e of the abutment 5 penetrates, at the latest in the final part of the insertion process, into the extension 6g of the hole 6e of the shell 6 and spreads the segments 6i of the shell 6 outward away from the axis 7. The originally cylindrical outer surface 6c forming a part of the outer boundary of the segments 6i is inclined slightly toward the axis 7 and is given a more or less conical shape, but is shown as a cylindrical surface in FIG. 2. As a result of the spreading of the segments 6i, their outer surfaces are additionally pressed, at least partly, against the conical inner surface 4i of the base 4.

Immediately after the abutment 5 is connected to the base 4 or after a healing phase permitting healing of the gingiva 2, a dental prosthesis 9 indicated by a dash-dot line and in simplified form in FIG. 2 can be fixed to the outer part 5b of the abutment 5. The end section 5i of the abutment 5 can project into the dental prosthesis 9 in such a way that the latter rests on the shoulder surface 5k. Otherwise, the dental prosthesis may have a screw which is not shown and which is screwed firmly into the threaded hole 5m.

If the base 4, the abutment 5 and the shell 6 are assembled according to FIG. 2 to give a device 3, and the thread part 5c of the abutment 5 is screwed through the hole 6e of the shell 6 to the internal thread 4g of the base 4, the shell 6 which is likewise screwed to the thread part 5c of the abutment 5 fits firmly in the extension 4h of the hole 4e of the base 4 and rests with the conical outer surface 6a against the conical inner surface 4i of the base. Furthermore, the outer part 5b of the abutment 5 rests with the conical stop surface 5g on the conical annular surface 4k of the base 4.

Although certain inaccuracies in manufacture can occur in the manufacture of the base 4, of the abutment 5 and of the shell 6 even in the case of high precision, both conical surfaces 4i and 4k of the base 4 rest tightly and firmly against the conical surfaces 6a and 5g of the shell 6 and of the abutment 5, respectively, in the assembled device. In addition, the segments 6i of the shell 6 which have been spread by the abutment 5 are firmly clamped between the abutment and the base. The abutment 5 is therefore connected in a very stable manner to the base 4, and the connection can in particular absorb both large compressive forces parallel to the axis 7 and large forces directed transverse to the axis 7 or can transmit said forces from the abutment to the base. The static frictional forces, compressive forces and clamping forces which are active between the various parts ensure in particular that the abutment itself does not unscrew from the base 4.

The conical annular surface 4k of the base 4 and the conical stop surface 5g of the abutment are completely rotationally symmetrical with respect to the axis 7 and are completely smooth around said axis, i.e. are not interrupted by slots or grooves or the like. The surfaces 4k, 5g therefore rest against one another, without gaps, around the axis 7 and the mouth of the hole 4e of the base 4. The covering section 5f furthermore covers the end face 4d of the base 4, which end face is present below the gingiva 2, up to the outer edge 4m of the annular surface 4k. The covering section 5f of the abutment abuts the edge 4m of the base 4 essentially without joints and without gaps. At the abutment point—i.e. at the edge 4m—the lateral surface sections 4r and 5h make an angle of between 135° and 180° and namely at least 150° with one another. As a result of this embodiment of the section 4c of the base 4 and of the abutment covering section 5f covering the latter, it is possible at least substantially to prevent cavities in which bacteria can develop from being formed under the gingiva 2 in the region of the end face 4d of the base during healing and growing together of the previously cut open gingiva 2.

FIG. 5 shows a jaw bone 1, a gingiva 2 and a device designated by 13. The latter has a base 4 which is identical or similar to that of the device 3 shown in FIG. 2. The abutment 5 of the device 13 can likewise be identical or similar to that of the device 3 and possesses in particular an essentially cylindrical thick part 5e. However, the device 13 has a shell 16 which differs from the shell 6 of the device 3. In the case of the shell 16, the conical outer surface 16a extends from the conical bevel 16b present at the lower end of the shell to the upper end of the shell 16. The latter thus has no outer surface corresponding to the cylindrical outer surface 6c. The shell 16 has an axial through-hole 16e which has an internal thread 16f at the bottom and, at the top, an extension 16g which is partly bordered or formed by a cylindrical inner surface. However, in contrast to the corresponding diameter of the shell 6, the diameter of this cylindrical inner surface is not smaller than the diameter of the cylindrical thick part 5e but at least equal to this last-mentioned diameter. Furthermore, no slots corresponding to the slots 6h are present in the shell 16, so that the lateral surface of the shell 16 completely encloses its axis everywhere.

When it is used, the device 13 can be assembled analogously to the device 3. Although the shell 16 of the device has no segments corresponding to the spreadable segments 6i of the shell 6, it still gives a stable connection between the abutment and the base. Since the shell 16 is formed in a somewhat simpler manner than the shell 6, it can be produced more economically than the latter. Otherwise, the device 13 has properties similar to those of the device 3.

Figure 6:
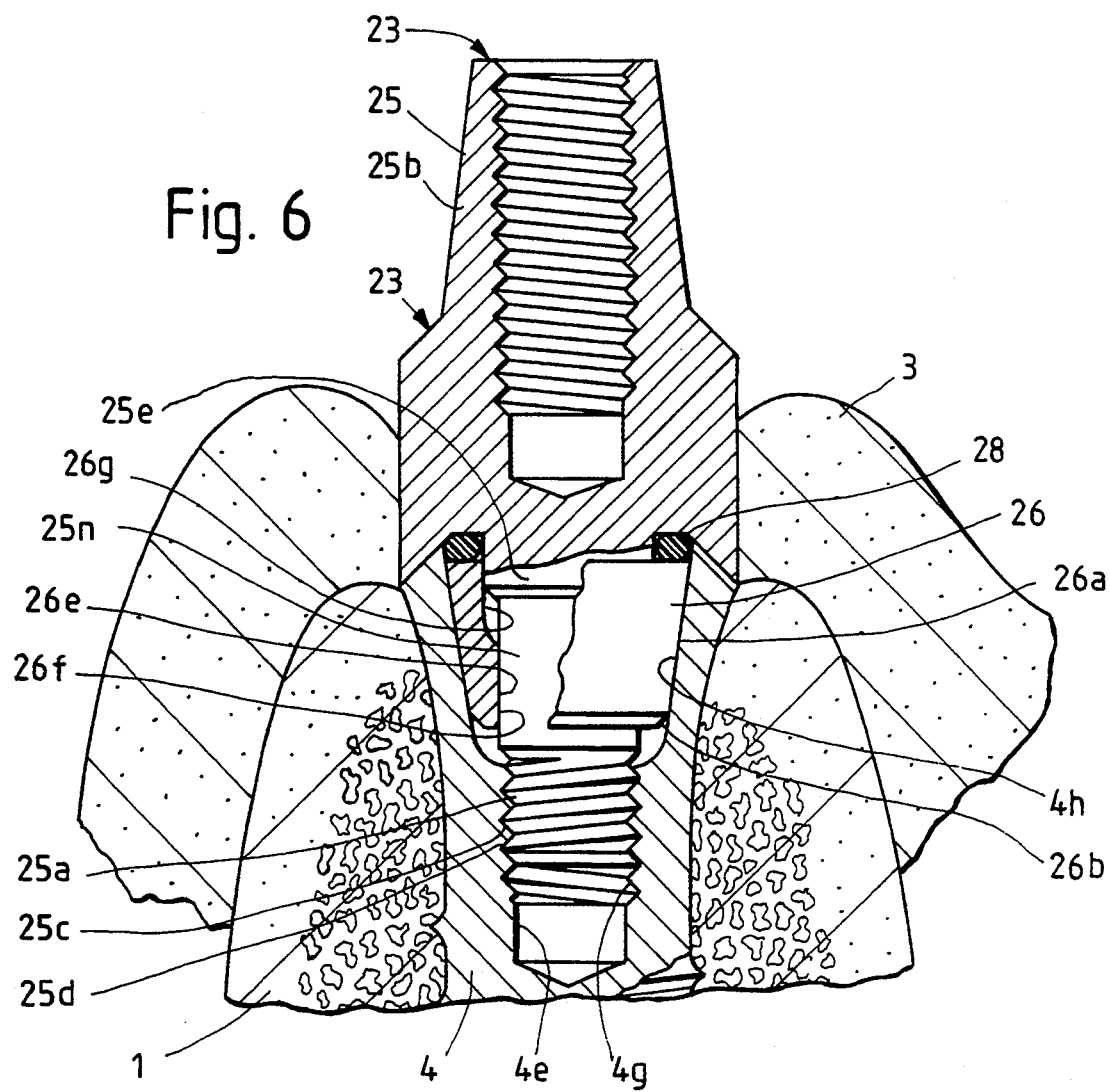
FIG. 6 shows a section, corresponding to FIG. 2, through a device having a shell of yet another design.

The device 23 shown in FIG. 6 has a base 4 which in turn is formed identically or similarly to that of the device 3 and in particular has a hole 4e with an internal thread 4g and an extension 4h. The abutment 25 of the device 23 has an inner part 25a and an outer part 25b. The inner part 25a has a thread part 25c with an external thread 25d and an essentially cylindrical thick part 25e. However, the abutment 25 differs from the abutment 5 in that the external thread 25d is shorter than the external thread 5d. While the latter extends, in the case of the abutment 5, almost to its thick part, the abutment 25 also possesses, between the external thread 25d and the thick part 25e, a threadless shaft 25n whose diameter is, for example, identical to the nominal or external diameter of the external thread 25d or only very slightly larger than the last-mentioned diameter.

The shell 26 belonging to the device 23 has a conical outer surface 26a which extends from a bevel 26b present at the thinner, lower end of the shell to the upper, further end of the shell 26. The shell 26 furthermore has an axial through-hole 26e. This has a smooth, i.e. threadless, cylindrical section 26f instead of the internal thread 6f of the shell 6. Its diameter is approximately equal to the diameter of the shaft 25n, so that the latter fits tightly, or with at most very little radial play, into the cylindrical section 26f. The hole 26e has an extension 26g above the section 26f. Said extension is partly formed by a cylindrical inner surface whose diameter is at least equal to the diameter of the cylindrical thick part 25e of the abutment 25. Otherwise, the shell 26 has no slots corresponding to the slots 6h of the shell 6.

The device 23 may additionally have an elastomeric ring 28 which may consist, for example, of a biocompatible, sterilizable, O-ring. This ring 28 may be arranged between that surface of the abutment 5 which covers the mouth of the hole 4e of the base 4 and the radial annular surface which faces said surface of the abutment 5 and is present at the further end of the shell 26.

On assembly of the device 23, the shell 26, for example in the state separated from the abutment 25, can be pressed into the extension 4h of the hole 4e of the base 4 and/or gently tapped into the extension 4h. Thereafter, the elastomeric ring 28 can be inserted into the top of the extension 4h and the thread part 25c of the abutment 25 can be screwed through the shell 26 and into the internal thread 4g of the base. That section of the inner part 25a which consists of the thick part 25e and the shaft 25n then passes through the shell 26. The shell 26 then furthermore rests with its conical outer surface 26a against the conical inner surface of the extension 4h, fits tightly into the latter and is moreover secured by the ring 28 against upward, axial displacements. In other respects, the device 23 has properties similar to those of the device 3.

FIG. 7 shows parts of a jaw bone 1, the gingiva 2 and a device 23. The latter has a base 4, an abutment 35 and a shell 6. The base 4, the inner part 35a of the abutment 35 and the shell 6 are identical or similar to those in the device 3. On the other hand, the outer part 35b of the abutment 35 differs from the outer part 5b of the abutment 5 and possesses, on that side of the cylindrical covering section 35f which is opposite the base 4, an end section having a multiedged peg 35i which, in an axial view, forms, for example, a regular octagon. A conical shoulder surface which tapers toward the multiedged peg 35i and together with the latter forms a shoulder is present between the covering section 35f and said peg. Otherwise, the abutment 35 is provided with a threaded blind hole 35m having a mouth in the end face of the multiedged peg.

FIG. 8 shows parts of a jaw bone 1, the gingiva 2 and a device 43. Its base 4 and shell 6 are identical to those in the device 3. The abutment 45 of the device 43 has an inner part 45a which is identical to that in the device 3. The outer part 45b of the abutment 45 has a cylindrical covering section 45f and, on its side opposite the base 4, a retentive anchor 45i and a neck 45m connecting said anchor to the remaining abutment. The covering section 45f has, on the side opposite the inner part 45a, a shoulder surface 45k which encloses the neck 45m, forms a shoulder together with said neck and has an inner, flat section which is at right angles to the axis 7 and a section which is inclined outward away from the retentive anchor and is, for example, conical.

In the device described with reference to FIGS. 1 to 8, the base 4 has a completely subgingival arrangement. On the other hand, the device shown in FIG. 9 has a base 4 which projects substantially out of the jaw bone and passes at least substantially through the gingiva 2 after the latter has healed, so that the end face of the base 4 is approximately flush with the boundary of the gingiva 2, which boundary is opposite the jaw bone 1, and/or is located outside the gingiva. Apart from its different, transgingival arrangement, the base 4 of the device 53 can be formed identically to the base of the devices 3, 13, 23, 33, 43 or may have a slightly longer cylindrical section 4a and a correspondingly longer external thread 4b. The abutment 55 of the device 53 has an inner part 55a which is identical to that in the abutment 5. The outer part 55b of the abutment 55 has a covering section 55f and a retentive anchor 55i connected to said covering section by a neck 45m. The covering section 55f has a shoulder surface 55k enclosing the neck 55m. The abutment 55 thus has a retentive anchor as in the case of the abutment 45, but differs from the latter in that its covering section 55f has a substantially shorter axial dimension than the covering section of the abutment 45. Furthermore, instead of a cylindrical lateral surface section, the covering section 55f has a lateral surface section which is arc-shaped in axial section and has, at its end located at the outer edge of the conical annular surface 4k of the base 4, an approximately continuous connection to the lateral surface of the base and, at the other end, goes over continuously into a flat section of the shoulder surface 55k, which section is at right angles to the axis 7. The shell of the device 53 is identical to that in the device 3.

The devices 43 and 53 having a retentive anchor 45$i$ and 55$i$, respectively, permit the fixing of a dental prosthesis with a closure element into which the retentive anchor can be detachably snapped similarly to a press stud closure. If a dental prosthesis not shown in FIGS. 8, 9 is detachably clipped to the abutments 45, 55, for example, a gap-like intermediate space may be present between said prosthesis and the shoulder surface 45$k$ or 55$k$. However, the shoulder surfaces 45$k$, 55$k$ may readily be so far away from the jaw bone that, in spite of the intermediate space mentioned, the gingiva scarcely goes over them and they can be readily cleaned. In other respects, the abutments 45, 55 are connected in a stable manner to the base 4—as explained in detail for the abutment 5.

The device 63 shown in FIG. 10 has a base 4, an abutment 65 and a shell 6. The base 4 is once again identical or similar to that of the device 3 but, analogously to the device 53, is inserted into a jaw bone 1 in such a way that it at least essentially penetrates the gingiva after the latter has healed. The shell 6 is identical to that in the device 3.

The abutment 65 has an inner part 65$a$ which is formed identically to that in the abutment 5. The outer part 65$b$ of the abutment 65 possesses a lateral surface section having an approximately continuous connection to the lateral surface of the base 4 and extending away therefrom and, at its end opposite the base 4, an end section 65$i$ which tapers, for example slightly conically, toward its free end and is provided with a recess 65$m$ in its end face. Said recess contains a magnetic coupling element 68 which consists of at least one originally separate member connected rigidly and preferably nondetachably to the remainder of the abutment 65. While the member forming the actual abutment 65 consists of non-magnetic titanium, the magnetic coupling element 68 is ferromagnetic and has at least one permanent magnet and/or at least one magnetically soft member. The abutment 65 of the device 63 serves for holding a dental prosthesis which is not shown in FIG. 10 and which likewise has a ferromagnetic coupling element which, in cooperation with the magnetic coupling element 68, permits a detachable connection between the dental prosthesis and the abutment 65. At least one of the two cooperating magnetic coupling elements must have a permanent magnet.

The device 73 shown in FIG. 11 has a base 4 projecting out of a jaw bone 1 and passing through the gingiva 2, a shell 6 and an abutment 75, the base 4, the shell 6 and the inner part 75$a$ of the abutment 75 being idetnical or similar to those in the device 3. The outer part 75$b$ of the abutment 75 has a covering section 75$f$ covering the end face of the base 4 and, at its end opposite the base, a shoulder surface 75$k$ making at least approximately a right angle with the axis 7 and a projection or continuation 75$i$ which projects away from said shoulder surface, is coaxial with the axis 7 and, for example, consists of a cylindrical pin. The projection or continuation 75$i$ can project into a dental prosthesis, which is not shown. The dental prosthesis or at least a part thereof can rest on the shoulder surface 75$k$ forming a shoulder together with the projection or continuation and can be soldered to the abutment 75 at said shoulder surface. The soldering process is preferably carried out with the abutment 75 separated from the base 4.

The devices 3, 13, 23, 33, 73 described with reference to FIGS. 1 to 7 and 11 can alternatively be used for fixing a dental prosthesis which has only a single artificial tooth or a plurality of artificial teeth. The devices 43 or 53 or 63 having a retentive anchor 45$i$, 55$i$ or a magnetic coupling element 68 are intended, together with at least one other device of the same type, for detachably fixing a dental prosthesis having a plurality of teeth, i.e. a bridge or a denture.

The jaw bone 1 shown in various Figures consists of a mandible from which the devices project on the upper side. However, the devices can also be inserted into a maxilla and then project downward from this.

Otherwise, a dentist or surgeon using devices can be provided with a set of bases 4 of different lengths and thicknesses so that the dentist or surgeon can select a base having a length and diameter adapted to the individual characteristics of the jaw bone. Similarly, abutments 5 having covering sections 5$f$ of different lengths can be provided so that a dentist or surgeon can select an abutment where the length of the covering section is adapted to the individual thickness of the gingiva. The same also applies to the abutments 25, 35, 45.

In the case of the base 4, the axial hole 4$n$ having a mouth at its end opposite the abutment, and the radial holes 4$p$, can be omitted. Furthermore, the external thread 4$b$ may be omitted in the base 4. Moreover, the base may be slightly angled so that the axis of the section 4$c$ widening in a trumpet-like manner and of the hole 4$e$ makes an angle with the axis of that end section of the base which is opposite the end face 4$d$.

Furthermore, features of different devices described can be combined with one another. For example, on the one hand a ring corresponding to the elastomieric ring 28 of the device 23 may also be provided in the device 13 shown in FIG. 5 or, on the other hand, the ring 28 can be omitted in the device 23. Moreover, the inner part of the abutment and the shells of the devices shown in FIGS. 7 to 11 could be similar to identical to those in the devices 13 or 23.

What is claimed is:

1. A device for fixing a dental prosthesis to a jaw bone, having a base intended for insertion into a hole in the jaw bone and an abutment which can be connected to the base and is intended for holding the dental prosthesis outside the jaw bone, the base having an end face, a hole with a mouth located at the end face, with an internal thread and with an extension widening from the internal thread to the end face and bordered at least partly by a conical inner surface, and having an annular surface enclosing the mouth of the hole, and the abutment possessing an inner part which is intended for being received in the hole of the base and has an external thread intended for screwing to the internal thread of the base, and an outer part nondetachably connected to the inner part and intended for extending outside the base, wherein a shell with an axial through-hole and with a conical outer surface intended to rest against the conical inner surface of the base is present, wherein the inner part of the abutment can be screwed through the hole with the internal thread of the base, and wherein the outer part of the abutment has a stop surface tapering inward away from the inner part and intended to rest against the annular surface of the base.

2. A device as claimed in claim 1, wherein the conical inner surface of the base and the conical outer surface of the shell make identical angles with an axis of the device.

3. A device as claimed in claim 2, wherein the conical inner surface of the base and the conical outer surface of the shell make angles of at least 5° and at most 15° with the axis.

4. A device as claimed in claim 1, wherein the annular surface and the stop surface make an angle of at least 20° and at most 70° with an axis of the device.

5. A device as claimed in claim 1, wherein the abutment has a smooth lateral surface section which is adjacent to a outer edge of the stop surface and whose axial dimension is at least 2 mm.

6. A device as claimed in claim 1, wherein the abutment is formed in order to cover the annular surface of the base up to the outer edge of said surface and wherein the base and the abutment have lateral surface sections which abut one another at the outer edge of the annular surface in the assembled device.

7. A device as claimed in claim 6, wherein the two abutting lateral surface sections make, with the annular surface, angles whose sum is 135° to 180°.

8. A device as claimed in claim 1, wherein the shell is divided into segments by slots at that end of its conical outer surface which has a larger diameter, and wherein the inner part of the abutment has, between its external thread and the outer part of the abutment, a thick part which has a larger diameter than the external thread and is formed in order to engage the segments when the abutment is screwed into the base and to spread said segments outward.

9. A device as claimed in claim 1, wherein the hole of the shell is provided, at least over a part of its length, with an internal thread which can be screwed with the external thread of the abutment.

10. A device as claimed in claim 1, wherein the base, the abutment and the shell each consists of a one-piece member.

11. A device as claimed in claim 1, wherein the outer part has a threaded hole having a mouth at its end opposite the inner part.

12. A device as claimed in claim 1, wherein the outer part has a multi-edged peg at its end opposite the inner part.

13. A device as claimed in claim 1, wherein the outer part has a retentive anchor at its end opposite the inner part.

14. A device as claimed in claim 1, wherein the outer part has, at its end opposite the inner part, a shoulder surface and a projection projecting away therefrom, and is adapted so that the dental prosthesis can be soldered onto the outer part.

15. A device as claimed in claim 1, wherein the outer part has a ferromagnetic coupling element at its end opposite the inner part.

16. A device as claimed in claim 1, wherein the annular surface of the base and the stop surface of the abutment are conical, encompasses the mouth of the base hole without interruption in an assembled condition of the device, and form identical angles with an axis of the device.

17. A device for fixing a dental prosthesis to a jaw bone having a hole, the device comprising:
a base to be received in the jaw bone hole and including a hole and an end surface, the hole of the base having a cylindrical hole portion having an internal thread, and a widened portion extending between the cylindrical hole portion and the end surface and having an outwardly tapering inner conical surface defining a mouth located at the end surface;
an abutment for supporting the dental prosthesis outside the jaw bone and detachably connected to the base, the abutment including an inner part having an external thread cooperating with the internal thread of the cylindrical hole portion of the base for connecting the abutment with the base, and an outer part to be located outside of the jaw bone for supporting the dental prosthesis and formed integrally with the inner part; and
a shell located in the widened portion of the stepped hole between the inner part of the abutment and the inner conical surface of the widened portion of the hole and having an outer conical surface resting against the inner conical surface of the widened portion;
wherein the base has an annular surface surrounding the mouth, and the outer part of the abutment has a stop surface for resting against the annular surface of the base.

18. A device as claimed in claim 17, wherein each of the base, the abutment, and the shell is formed as a one-piece member.

19. A device as claimed in claim 17, further comprising means for urging the shell against the inner conical surface of the widened portion of the hole.

20. A device as claimed in claim 19, wherein said urging means comprises an elastomeric ring located between a surface of the inner part of the abutment and the shell.

21. A device as claimed in claim 17, wherein the shell has a hole provided at least over a part of a length thereof with an internal thread which cooperates with the external thread of the inner part of the abutment.

22. A device for fixing a dental prosthesis to a jaw bone, having a base intended for insertion into a hole in the jaw bone and an abutment which can be connected to the base and is intended for holding the dental prosthesis outside the jaw bone, the base having an end face, a hole with a mouth located at the end face, with an internal thread and with an extension widening from the internal thread to the end face and bordered at least partly by a conical inner surface, and having an annular surface enclosing the mouth of the hole, and the abutment possessing an inner part which is intended for being received in the hole of the base and has an external thread intended for screwing to the internal thread of the base, and an outer part intended for extending outside the base, wherein a shell with an axial through-hole and with a conical outer surface intended to rest against the conical inner surface of the base is present, wherein each of the base, the abutment, and the shell is formed as a one-piece member, wherein the inner part of the abutment can be screwed through the hole with the internal thread of the base, and wherein the outer part of the abutment has a stop surface tapering inward away from the inner part and intended to rest against the annular surface of the base.

23. A device as claimed in claim 22, wherein the shell is divided into segments by slots at that end of its conical outer surface which has a larger diameter, and wherein the inner part of the abutment has, between the external thread and the outer part of the abutment, a thick part which has a larger diameter than the external thread and is formed for engaging the segments when the abutment is screwed into the base and to spread the segments outward.

24. A device as claimed in claim 22, wherein the hole of the shell is provided, at least over a part of its length, with an internal thread which can be screwed with the external thread of the inner part of the abutment.

25. A device as claimed in claim 22, wherein the annular surface of the base and the stop surface are conical, encompass the mouth of the base hole without interruption in an assembled condition of the device, and form identical angles with a longitudinal axis of the device.

26. A device for fixing a dental prosthesis to a jaw bone, having a base intended for insertion into a hole in the jaw bone and an abutment which can be connected to the base and is intended for holding the dental prosthesis outside the jaw bone, the base having an end face, a hole with a mouth located at the end face, with an internal thread and with an extension widening from the internal thread to the end face and being bordered at least partly by a conical inner surface, and having an annular surface enclosing the mouth of the hole, and the abutment possessing an inner part which is intended for being received in the hole of the base and has an external thread intended for screwing to the internal thread of the base and an outer part nondetachably connected to the inner part and intended for extending outside the base, wherein a shell with an axial through-hole and with a conical outer surface intended to rest against the conical inner surface of the base is present, wherein a means intended for urging the shell against the inner conical surface of the extension is provided, wherein the inner part of the abutment can be screwed through the hole with the internal thread of the base, and wherein the outer part of the abutment has a stop surface tapering inward away from the inner and intended to rest against the annular surface of the base.

27. A device as claimed in claim 26, wherein the urging means comprises an elastomeric ring located between the surface of the outer part and the shell for urging the shell away from the outer part and against the inner conical surface of the extension.

28. A device for fixing a dental prosthesis to a jaw bone, having a base intended for insertion into a hole in the jaw bone and an abutment which can be connected to the base and is intended for holding the dental prosthesis outside the jaw bone, the base having an end face, a hole with a mouth located at the end face, with an internal thread and with an extension widening from said internal thread to the end face and bordered at least partly by a conical inner surface, and having an annular surface enclosing the mouth of the hole, and the abutment possessing an inner part which is intended for being received in the hole of the base and has an external thread intended for screwing to the internal thread of the base and an outer part nondetachably connected to the inner part and intended for extending outside the base, wherein a shell with an axial through-hole and with a conical outer surface intended to rest against the conical inner surface of the base is present, wherein the inner part of the abutment can be screwed through the hole with the internal thread of the base, wherein the outer part of the abutment has a stop surface tapering inward away from the inner part and intended to rest against the annular surface of the base, and wherein the hole of the shell is provided, at least over a part of its length, with an internal thread which can be screwed with the external thread of the internal part of the abutment.

29. A device as claimed in claim 28 wherein the shell is divided into segments by slots at that end of its conical outer surface which has a larger diameter, and wherein the inner part of the abutment has, between its external thread and the outer part of the abutment, a thick part which has a larger diameter than the external thread and is formed in order to engage the segments when the abutment is screwed into the base and to spread the segments outward.

30. A device as claimed in claim 28, wherein said the annular surface of the base and the stop surface of the abutment are conical, encompass the mouth of the base hole without interruption in an assembled condition of the device, and form identical angles with an axis of the device.

31. A device as claimed in claim 28, wherein the annular surface and the stop surface of the abutment make an angle of at least 20° and at most 70° with an axis of the device.

* * * * *